United States Patent [19]

Leibovic

[11] Patent Number: 5,735,806
[45] Date of Patent: Apr. 7, 1998

[54] WRIST TRACTION APPARATUS

[76] Inventor: Stephen J. Leibovic, 11221 Fanwood Ct., Richmond, Va. 23233

[21] Appl. No.: 605,703

[22] Filed: Feb. 23, 1996

[51] Int. Cl.$^6$ .................................................. A61F 5/04
[52] U.S. Cl. .................... 602/32; 602/35; 602/36; 128/578; 24/136 R; 24/115 M
[58] Field of Search ................... 601/23, 40; 128/845, 128/878, 879, 880; 602/20, 21, 31–36; 248/925; 182/5, 192; 24/136 R, 136 C, 115 M

[56] References Cited

U.S. PATENT DOCUMENTS

| | | |
|---|---|---|
| 454,760 | 6/1891 | Osborne .................................. 24/136 R |
| 2,014,111 | 9/1935 | Longfellow . |
| 2,034,680 | 3/1936 | Longfellow . |
| 2,243,294 | 5/1941 | Stearns . |
| 2,515,590 | 7/1950 | Chaffin . |
| 2,590,739 | 3/1952 | Wagner et al. . |
| 2,783,758 | 3/1957 | Trott . |
| 3,850,166 | 11/1974 | Tamny et al. . |
| 4,445,506 | 5/1984 | Johansson et al. . |
| 4,523,583 | 6/1985 | Noble ..................................... 606/241 |
| 4,616,637 | 10/1986 | Caspari et al. . |
| 4,809,605 | 3/1989 | Rosendale . |
| 4,837,874 | 6/1989 | Giercarz et al. ......................... 5/84.1 |
| 4,887,325 | 12/1989 | Tesch ...................................... 24/136 L |
| 5,027,802 | 7/1991 | Donohue . |
| 5,074,291 | 12/1991 | Carter . |
| 5,123,131 | 6/1992 | Sandravovic ........................... 5/81.1 |
| 5,127,898 | 7/1992 | McConnell . |
| 5,345,947 | 9/1994 | Fisher ..................................... 128/878 |
| 5,387,186 | 2/1995 | Edland .................................... 606/241 |
| 5,441,480 | 8/1995 | Kane et al. . |
| 5,451,202 | 9/1995 | Miller et al. . |

FOREIGN PATENT DOCUMENTS 214540   9/1988   Japan .................................. 24/115 M

OTHER PUBLICATIONS

PETZL, *Croll B06*, Z.I. Crolles, France Jan. 29, 1995.

*Primary Examiner*—Jeanne M. Clark
*Attorney, Agent, or Firm*—Barnes & Thornburg

[57] ABSTRACT

An apparatus for applying a traction force to an appendage of a subject which includes a one-way gripping device having a channel and a cam. The cam is pivotal so that a gripping surface of the cam can be positioned in the channel. A force applicator which can be a rope or cable extends through the channel of the one-way gripping device. The force applicator is free to slide through the channel of the one-way gripping device in one direction, but is gripped by the cam and prevented from moving in an opposite direction. One end of the force applicator is secured to an appendage of a subject. A traction force is applied to the appendage by pulling the force applicator through the one-way gripping device.

20 Claims, 2 Drawing Sheets

WRIST TRACTION APPARATUS

TECHNICAL FIELD

The present invention relates to a traction apparatus and more particularly to a wrist traction apparatus for use in wrist surgery.

BACKGROUND ART

Surgical procedures are commonly used to repair fractures of the bones of the hand and forearm, tears to tendons and ligaments, and other trauma to the hand, wrist and forearm. Due to the large number of bones, tendons, ligaments, and muscles in the hand and forearm, surgical procedures affecting these areas require a high degree of precision.

Surgical procedures on the hand, wrist and forearm are facilitated by devices which maintain skeletal and muscular structures in appropriate states of traction. In particular, surgical procedures to repair fractured bones of the hand, wrist and forearm are most often preformed with the fractured bones in a "reduced" or corrected position throughout the surgical procedure.

There are a number of devices which are designed to properly position and apply traction to hands, wrists and forearms during surgery. Some commonly used devices are exemplified by U.S. Pat. No. 5,074,291 to Carter and U.S. Pat. No. 4,445,506 to Johansson et al.

The Carter patent discloses a hand traction surgical table upon which the arm of a patient is supported horizontally during surgery. Tension to the hand, wrist and forearm is applied by fitting finger traps onto selected fingers of the patient and connecting the finger traps to an appropriate weight via a cable and pulley arrangement.

The Johansson et al. patent is directed to an apparatus which maintains the forearm of a patient in a vertical position. The apparatus of Johansson et al. utilizes a crank device in combination with a limb retaining means to apply tension to the patient's arm.

Other traction devices are described in U.S. Pat. Nos. 5,451,202 to Miller et al., 5,441,480 to Kane et al., 5,127, 898 to McConnell, 5,027,802 to Donohue, 4,890,605 to Rosendale, 4,616,637 to Caspari et al., 3,850,166 to Tamny et al., 2,590,739 to Wagner et al., 2,515,590 to Chaffin, 2,243,294 to Stearns, 2,034,680 to Longfellow, and 2,014,111 to Longfellow.

Precautions must be taken to ensure that devices used during surgical procedures are sterilized. This may require actual sterilization of an apparatus and/or covering the apparatus with a sterilized covering. A large, complicated apparatus may be difficult or impractical to sterilize and difficult to easily cover. In addition, large apparatus may become obstacles which have to be negotiated during a surgical procedure.

The present invention is directed to a traction apparatus which is simple to use, uncomplicated and advantageous over existing traction devices.

DISCLOSURE OF THE INVENTION

It is accordingly one object of the present invention to provide an apparatus for applying traction to an appendage of a subject.

It is another object of the present invention to provide an apparatus for applying traction to an appendage of a subject which is simple to operate.

Another object of the present invention is to provide an apparatus for applying traction to an appendage of a subject which can be used in surgical procedures.

Another object of the present invention is to provide an apparatus for applying traction to a subject's forearm for surgical procedures.

A further object of the present invention is to provide a method of applying traction to an appendage of a subject.

A further object of the present invention is to provide a method of applying traction to an appendage of a subject during a surgical procedure.

A still further object of the present invention is to provide a method of applying traction to the forearm of a subject for purposes of performing surgery thereon.

According to these and further objects of the present invention which will become apparent as the description thereof proceeds below, the present invention provides an apparatus for applying a traction force to an appendage of a subject which includes:

a one-way gripping device having a channel and a cam, the cam including a gripping surface and being pivotal so that the gripping surface of the cam can be positioned in:

an operable position in which the gripping surface is in the channel and, an open position in which the cam is out of the channel;

a force applicator which extends through the channel of the one-way gripping device and includes a free end and a force applying end; and means to secure the force applying end of the force applicator to an appendage of a subject.

The present invention further provides a method for applying a traction force to an appendage of a subject which involves:

securing a force applicator to an appendage of a subject;

positioning a length of the force applicator in a channel of a one-way gripping device which allows the force applicator to slide freely in a first direction in the channel while preventing the force applicator from moving in a second direction in the channel;

attaching the one-way gripping device to a stationary structure; and pulling the force applicator through the one-way gripping device in the first direction to apply a traction force to the appendage.

The present invention also provides an improved method of applying traction forces during hand surgery procedures which involves:

securing a force applicator to an appendage of a subject's forearm;

positioning a length of the force applicator in a channel of a one-way gripping device which allows the force applicator to slide freely in a first direction in the channel while preventing the force applicator from moving in a second direction in the channel;

attaching the one -way gripping device to a stationary structure; and pulling the force applicator through the one-way gripping device in the first direction to apply a traction force to the subject's forearm.

BRIEF DESCRIPTION OF DRAWINGS

The present invention will be described hereafter with reference to the attached drawings which are given as non-limiting examples only, in which.

BEST MODE FOR CARRYING OUT THE INVENTION

The present invention provides a traction apparatus which can be used to apply a traction force to an object. The traction apparatus includes a one-way gripping device which allows a force applicator such as a rope or cord to be selectively positioned therein. In use, the one-way gripping device is secured in a stationary manner and the force applicator is selectively position therein in a one-way sliding manner. The one-way gripping device adapted for use in the present invention is a type of ascender which is conventionally used by mountain climbers, an example of which is the Croll B06, manufactured by Z. I. Crolles, France.

The force applicator is connected to the object to which traction force is to be applied. In the case of a hand, the force applicator can be connected to selected fingers of the hand utilizing conventional finger traps. In the case of an arm or leg, the force applicator can be connected to the arm or leg by a suitable sling or cuff.

The apparatus of the present invention provides a simple design which is particularly adaptable to hand and wrist surgery. However, it will be apparent that the design and concept of the present invention is not limited to hand and wrist surgery.

The present invention is simple in design and operation and compact so that it does not require excessive space when used. This is a particular advantage in operating rooms where obstacles which obstruct members of surgical teams are to be avoided. The present invention can also be constructed mainly of sterilizable materials or disposable parts, thus avoiding the need to be draped when used in surgical procedures.

Figure 1:
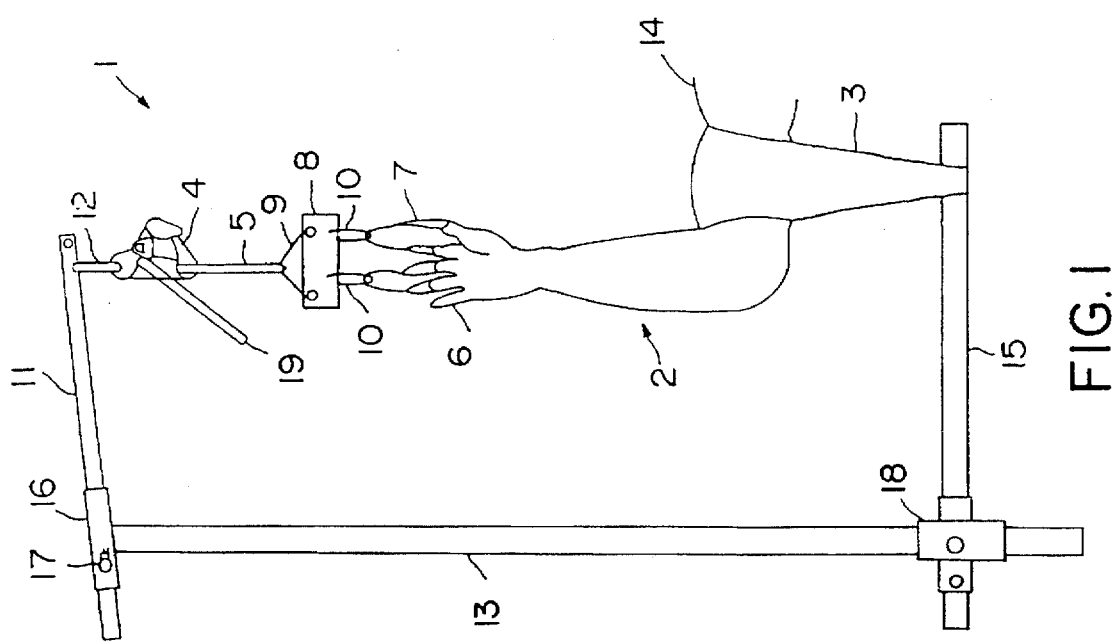
FIG. 1 is a plan view of the traction apparatus according to one embodiment of the present invention.

FIG. 1 is a plan view of the traction apparatus according to one embodiment of the present invention. In FIG. 1 the traction apparatus 1 is shown as being used to apply a traction force to a patient's forearm 2 with the apparatus and forearm of the patient in a vertical position. This orientation requires a sling 3 which secures the patient's arm against the traction force applied by the device of the present invention. It will be apparent to those skilled in the art that the present invention is not limited to use in any particular orientation. That is, the traction apparatus of the present invention could easily be used to apply a traction force to a patient's arm orientated horizontally, as depicted for example in U.S. Pat. No. 5,074,291 to Carter. It is further to be understood that the traction apparatus of the present is not limited for use in connection with hand and wrist surgery procedures, but could be used to apply traction forces to any appendage for surgical or nonsurgical treatment.

As shown in FIG. 1 the traction apparatus 1 of the present invention includes a one-way gripping device 4, a force applicator 5, and a means to attach the force applicator 5 to an object(s) to which a traction force is to be applied. In the embodiment shown in FIG. 1, the traction force is applied to the fingers 6 of a patient and the means to attach the force application to the patient's fingers 6 includes several finger traps 7 of conventional design. The finger traps 7 are attached to the force applicator 5 by means of a force distribution plate 8. The force distribution plate 8 distributes the traction force applied by the force applicator 5 to each of the finger traps 7.

In the embodiment of the invention shown in FIG. 1 the force distribution plate 8 is connected to one end of the force applicator 5 by means of a cable 9 which can freely slide with respect to the end of the force applicator 5 to thus balance or distribute the force transferred from the force applicator 5 to the finger traps 7. The finger traps 7 are slidingly attached to the distribution plate 8 through hooks or shackles 10. Although FIG. 1 shows the thumb and three fingers of the patient's hand being connected to the force distribution place 8, other combinations of one, two, or more digits could be connected to the force distribution plate 8 as desired, utilizing appropriate interconnections to distribute applied forces.

In FIG. 1 the one-way gripping device 4 is secured to an upper horizontal support 11 by a hook or shackle 12 so as to be stationary with respect to the patient's arm. The upper horizontal support 11 is connected to a vertical support 13, which can be for example an intravenous pole. In order to retain movement of the patient's arm, the upper arm 14 is secured to a lower horizontal support 15 by a sling 3. In the embodiment of the invention shown in FIG. 1 the upper and lower horizontal supports 11 and 15 may be intravenous pole attachments.

For convenience, the position of the upper horizontal support 11 is slidingly adjustable with respect to the vertical support 13 by means of a connector 16 at the top of the vertical support 13 in which the upper horizontal support 11 can slide and be secured by a fastener 17. Likewise, a two-directional sliding connector 18 is provided to receive both the lower horizontal support 15 and the vertical support 13, so that the height and length of the lower horizontal support 15 can be adjusted as desired.

FIG. 1 shows the one-way gripping device 4 as being secured in a stationary manner to a horizontal support 11. In alternative embodiments, the one-way gripping device 4 could be secured to any stationary support. FIG. 1 depicts an embodiment of the present invention which positions a patient's forearm vertically. The traction apparatus of the present invention could also be used to apply a traction force to a patient's arm orientated horizontally. In such a case all that is required is a means, e.g. a hook, for securing the one-way gripping device 4 to an operating table or side table. When used to apply a traction force to a patient's arm orientated horizontally, it is not necessary to include a sling to retain the patient's upper arm.

The force applicator 5 can be a rope, cord, cable, or the like, which is capable of sliding through the one-way gripping device 4 and being gripped thereby. The force applicator 5 extends through the one-way gripping device 4 as shown in FIG. 1. When the free end 19 of the force applicator 5 is pulled upward as shown in FIG. 1, the force applicator 5 slides in the one-way gripping device so as to apply a corresponding traction force to the patient's forearm. The one-way gripping device 4 allows the force applicator 5 to slide therethrough in one direction, but grips the force applicator 5 and prevents the force applicator 5 from moving therethrough in an opposite direction. This manner of operation will be discussed in more detail below.

The one-way gripping device 4, force distribution plate 8, finger traps 7, cable 9, and hooks or shackles 10 can all be made out of sterilizable materials such as autoclavable metals. The force applicator 5 can likewise be a metal cable which can be sterilized. In a preferred embodiment, a cord or rope is used as the force applicator 5. In this embodiment the force applicator can be sterilized or discarded after use to prevent contamination.

Figure 2A:
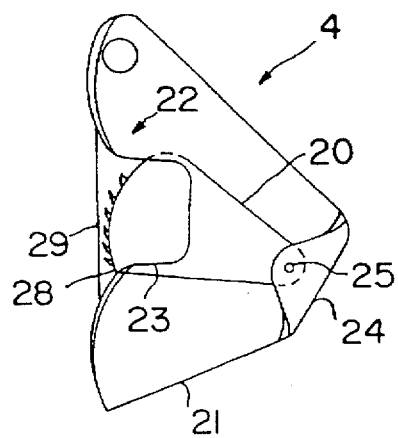
FIG. 2a is a plan view of one embodiment of the one-way gripping device used in the traction apparatus of the present invention which shows the gripping cam in its operable position.
Figure 2B:
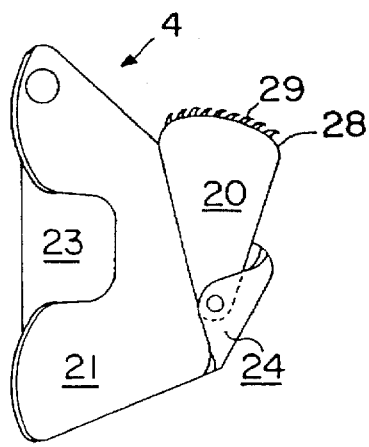
FIG. 2b is a plan view of the one-way gripping device of FIG. 2a which shows the gripping cam in its open position.

FIG. 2a is a plan view of one embodiment of the one-way gripping device 4 used in traction apparatus of the present invention with the gripping cam 20 in its operable position. The basic elements of the one-way gripping device 4 include a body 21 which provides a channel 22 through which the force applicator 5 can slide and a gripping cam 20 which is pivotally attached to the body 21 so as to pivot between an operable position as depicted in FIG. 2a and an open position as depicted in FIG. 2b. For simplicity, the body 21 shown throughout the drawings is preferably formed from a single piece of metal, having two protrusions which are bent at 180°. One bent protrusion 23 forms channel 22 through which the force applicator 5 slides. The other bent protrusion 24 forms a yoke structure in which gripping cam 20 can be pivotally attached by a pin element 25.

FIG. 2b is a plan view of the one-way gripping device 4 of FIG. 2a with the gripping cam 20 in its open position. In order to insert the force applicator 5 in the channel 22 of the one-way gripping device 4, the gripping cam 20 is pivoted away from channel 22 to the open position shown in FIG. 2b. As shown in FIG. 2b, the bent structure of protrusion 25 can be used as an abutment to stop gripping cam 20 from pivoting beyond it's open position.

Figure 2C:
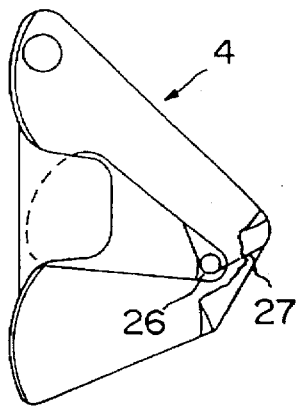
FIG. 2c is a cut-away plan view of the one-way gripping device of FIG. 2a which shows details of the gripping cam.

FIG. 2c is a cut-away plan view of the one-way gripping device 4 of FIG. 2a which shows details of the gripping cam 20. Desired movement of the gripping cam 20 can be achieved by gravitational forces when the gripping device 4 is properly orientated. In order to ensure proper movement of the gripping cam 20 in all orientations of the one-way gripping device 4, a spring biased force can be applied to the gripping cam 20. In FIG. 2c, the pivotal end of the gripping cam 20 is shown as having a slot 26 formed therein into which a spring member 27 can be attached and positioned about the pin 25 so as to apply a bias force between the gripping cam 20 and an inner surface of bent protrusion 24. This spring biased force ensures proper movement of the gripping cam 20 towards channel 22 so that the gripping surface 28 of the gripping cam 20 will be forced to contact a forced applicator 5 which is positioned in channel 22. Other spring arrangements, such as a coil spring, could be used to bias gripping cam 20.

As shown in FIGS. 2a and 2b, the gripping surface 28 of the gripping cam 20 includes teeth 29 which can grip into the force applicator 5 and prevent one-way movement of the force applicator 5 in channel 22. As depicted, teeth 29 are preferably orientated (angled) to grip a force applicator 5 in one direction and allow the force applicator 5 to freely slide in channel 22 in an opposite direction.

Figure 2D:
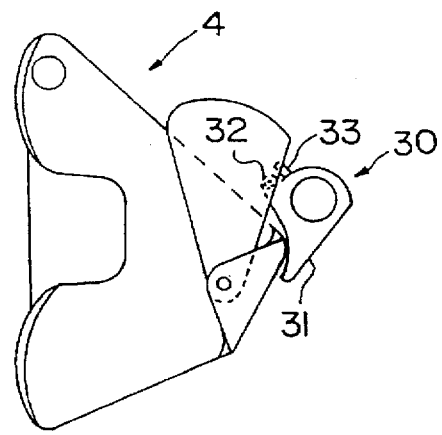
FIG. 2d is a plan view of another embodiment of the one-way gripping device of the present invention which includes a locking mechanism for holding the gripping cam in its open position.

FIG. 2d is a plan view of another embodiment of the one-way gripping device 4 of the present invention which includes a locking mechanism 30 for holding the gripping cam 20 in its open position. When spring member 27 is included to apply a biasing force to gripping cam 20, it has been found to be convenient to include a locking mechanism to secure the gripping cam 20 in its open position when inserting a force applicator 5 in the one-way gripping device 4. Such a locking mechanism 30 is shown in FIG. 2d. The locking mechanism 30 includes a hook structure 31 which is pivotally attached to gripping cam 20. When gripping cam 20 is in its open position as shown in FIGS. 2b and 2d, the hook structure 31 can pivot as shown in FIG. 2d so as to engage the outer surface of bent protrusion 24 or another part of body 21. The locking mechanism 30 is released from engagement with protrusion 24 by pivoting the hook structure 31 about pivot pin 32. As in the case of gripping cam 20, the hook structure 31 can be spring biased. For example, a coil spring 33 can extend between small protrusions or bores provided on the hook structure 31 and gripping cam 20 at a position adjacent pivot pin 32. In an alternative embodiment, the locking mechanism may include a hook structure which pivots about protrusion 24 and engages gripping cam 20.

Figure 3A:
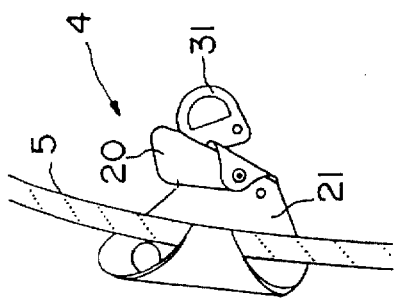
FIG. 3a is a plan view of the one-way gripping device of the present invention having a force applicator secured therein.

FIG. 3a is a plan view of the one-way gripping device of the present invention having a force applicator 5 secured therein. FIG. 3a shows a force applicator 5 positioned in channel 22 of the one-way gripping device 4 with the gripping cam 20 in its operable position. In the arrangement shown in FIG. 3a, force applicator 5 can slide freely upward in channel 22 in the direction of arrow "a". Movement of the force applicator 5 in this direction will cause the gripping cam 20 to pivot toward its open position. The one-way gripping device 4 will prevent the force applicator 5 from moving in an opposite direction to arrow "a", because gripping cam 20 will engage the force applicator 5 causing gripping cam 20 to press force applicator 5 between an inner surface of channel 22 and the gripping surface 28 of the gripping cam 20.

Figure 3B:
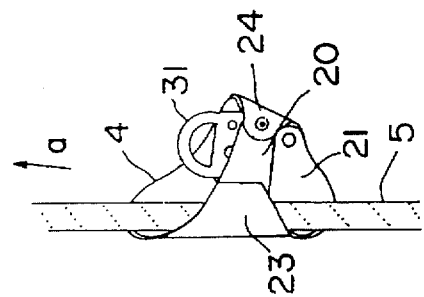
FIG. 3b is a plan view of the one-way gripping device of FIG. 3a with the gripping cam in its open position.

FIG. 3b is a plan view of the one-way gripping device 4 of FIG. 3a with the gripping cam 20 in its open position. FIG. 3b depicts how the force applicator 5 can be easily inserted into channel 22 when the gripping cam 20 is in its open position.

In use, a suitable apparatus, e.g. finger trap(s), cuff, sling, etc. is used to secure one end of the force applicator to a limb or appendage of a patient. If multiple apparatus are used, such as several finger traps, a force distribution means is provided between the apparatus and the force applicator. The gripping cam of the one-way gripping device is moved into its open position and the force applicator is positioned in the channel of the one-way gripping device. The gripping cam is then allowed to move into its operable position in which it engages the force applicator. The one-way gripping device is secured to a stationary supporting structure. The free end of the force applicator is pulled to apply a desired traction force to the patient. The traction force can be increased as desired by pulling on the free end of the force applicator. Traction force can be released at any time by pulling gripping cam toward its opened position so as to release the force applicator.

The present invention has been found to be particularly useful in hand and wrist surgery procedures, where traction can be applied without the use of pulleys and weights, and similar systems which are awkward to use and work around in an operating room.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed:

1. An apparatus for applying a traction force to an upper extremity of a subject which comprises:

a one-way gripping device having a channel and a cam, said channel having a central axis;

a force applicator which extends through said channel along said central axis and includes a free end and a force applying end; and means to secure said force applying end of said force applicator to an upper extremity of a subject which means to secure transmits a tensioning force to the upper extremity, said cam including a gripping surface and being pivotal so that said gripping surface of said cam can be positioned in:

an operable position in which said gripping surface is in said channel and cooperates with a portion of said channel to engage a force applicator positioned in said channel and, an open position in which said cam is out of said channel, wherein when said cam is in said operable position it is configured to allow said force applicator to be pulled in a direction away from the subject, thus applying traction while preventing said force applicator from slipping back twoard the subject, thus when said cam is in said open position said force applicator can freely move through said channel in either direction, and wherein said apparatus is sized and configured to be sterilizable for surgical use.

2. An apparatus for applying a traction force to an upper extremity of a subject according to claim 1, wherein said force applicator is a rope or cable.

3. An apparatus for applying a traction force to an upper extremity of a subject according to claim 1, wherein said means to secure comprises at least one finger trap.

4. An apparatus for applying a traction force to an upper extremity of a subject according to claim 3, wherein said means to secure comprises two or more finger traps.

5. An apparatus for applying a traction force to an upper extremity of a subject according to claim 4, further comprising force distribution means provided between said force applying end of said force applicator and said securing means.

6. An apparatus for applying a traction force to an upper extremity of a subject according to claim 5, wherein said force distribution means comprises a force distribution plate.

7. An apparatus for applying a traction force to an upper extremity of a subject according to claim 1, further comprising means to secure said one-way gripping device in a stationary manner so that a vertical traction force is applied to the upper extremity.

8. An apparatus for applying a traction force to an upper extremity of a subject according to claim 7, wherein said means to secure said one-way gripping device in a stationary manner comprises a horizontal support member.

9. An apparatus for applying a traction force to an upper extremity of a subject according to claim 7, further comprising means to restrain a portion of the upper extremity against an applied traction force.

10. An apparatus for applying a traction force to an upper extremity of a subject according to claim 1, further comprising means to secure said one-way gripping device in a stationary manner so that a horizontal traction force is applied to the upper extremity.

11. An apparatus for applying a traction force to an upper extremity of a subject according to claim 1, wherein said gripping surface includes a plurality of teeth.

12. An apparatus for applying a traction force to an upper extremity of a subject according to claim 1, further comprising means for applying a biasing force to said cam which biasing force urges said cam toward said operable position.

13. An apparatus for applying a traction force to an upper extremity of a subject according to claim 12, further comprising locking means for locking said cam into said open position.

14. An apparatus for applying a traction force to an upper extremity of a subject according to claim 13, wherein said locking means comprises a pivotal hook structure.

15. A method for applying a traction force to an upper extremity, of a subject which comprises:

providing an apparatus for applying a traction force to an upper extremity of a subject, said apparatus including:
a) a one-way gripping device having a channel and a cam, said channel having a central axis;
b) a force applicator which extends through said channel along said central axis and includes a free end and a force applying end: and
c) means to secure said force applying end of said force applicator to an upper extremity of a subject which means to secure transmits a tensioning force to the upper extremity, said cam including a gripping surface and being pivotal so that said gripping surface of said cam can be positioned
I) an operable position in which said gripping surface is in said channel and cooperates with a portion of said channel to engage a force applicator positioned in said channel; and
ii) an open position in which said cam is out of said channel, wherein when said cam is in said operable position it is configured to allow said force applicator to be pulled in a direction away from the subject thus applying traction while preventing said force applicator from slipping back toward the subject, and when said cam is in said open position said force applicator can freely move through said channel in either direction, and wherein said apparatus is sized and configured to be sterilizable for surgical use; securing said force applicator to an under extremity of a subject;

attaching said apparatus to a stationary structure; and pulling said force applicator through said one-way gripping device in said direction away from the subject to apply a traction force to said upper extremity.

16. A method for applying a traction force to an upper extremity of a subject according to claim 15, wherein said force applicator is secured to at least one finger of a subject by means of a finger trap.

17. A method for applying a traction force to an upper extremity of a subject according to claim 16, said at least one finger comprises a plurality of fingers and said method further comprising distributing the force applied to each of said plurality of fingers.

18. A method for applying a traction force to an upper extremity of a subject according to claim 15, wherein vertical traction force is applied to said upper extremity.

19. A method for applying a traction force to an upper extremity of a subject according to claim 15, wherein a horizontal traction force is applied to said upper extremity.

20. In a method of preforming hand surgery which includes applying a traction force to a subject's forearm, the improvement comprising:

providing an apparatus for applying a traction force to an upper extremity of a subject, said apparatus including;
 a) a one-way gripping device having a channel and a cam, said channel having a central axis
 b) a force applicator which extends through said channel along said central axis and includes a free end and a force applying end; and
 c) means to secure said force applying end of said force applicator to an upper extremity of a subject which means to secure transmits a tensioning force to the upper extremity, said cam including a gripping surface and being pivotal so that said gripping surface of said cam can be positioned in;
 I) an operable position in which said gripping surface is in said channel and cooperates with a portion of said channel to engage a force applicator positioned in said channel, and
 ii) an open position in which said cam is out of said channel, wherein when said cam is in said operable position it is configured to allow said force applicator to be pulled in a direction away from the subject, thus applying traction while preventing said force applicator from slipping back toward the subject, and when said cam is in said open position said force applicator can freely move through said channel in either direction, and wherein said apparatus is sized and configured to be sterilizable:

securing said force applicator to an upper extremity of said subject's forearm;

attaching said apparatus to a stationary structure; and pulling said force applicator through said one-way gripping; device in said direction.

* * * * *